US007538196B2

(12) United States Patent
Jung

(10) Patent No.: US 7,538,196 B2
(45) Date of Patent: May 26, 2009

(54) BISPECIFIC ANTIBODY MOLECULE

(76) Inventor: Gundram Jung, Schwabstrasse 30, 72108 Rottenburg-Wendelsheim (DE)

( * ) Notice: Subject to any disclaimer, the term of this patent is extended or adjusted under 35 U.S.C. 154(b) by 221 days.

(21) Appl. No.: 10/495,664

(22) PCT Filed: Nov. 9, 2002

(86) PCT No.: PCT/EP02/12545

§ 371 (c)(1),
(2), (4) Date: Apr. 4, 2005

(87) PCT Pub. No.: WO03/042231

PCT Pub. Date: May 22, 2003

(65) Prior Publication Data

US 2005/0244416 A1 Nov. 3, 2005

(30) Foreign Application Priority Data

Nov. 12, 2001 (DE) ................. 101 56 482

(51) Int. Cl.
*C07K 16/00* (2006.01)
*C07K 16/28* (2006.01)
*C07K 16/30* (2006.01)
*C07K 16/46* (2006.01)
*A61K 39/395* (2006.01)

(52) U.S. Cl. ............ 530/387.3; 530/388.2; 530/388.75; 424/136.1

(58) Field of Classification Search .................. None
See application file for complete search history.

(56) References Cited

U.S. PATENT DOCUMENTS

| 6,051,230 | A | * | 4/2000 | Thorpe et al. ............. 424/178.1 |
| 6,093,399 | A | * | 7/2000 | Thorpe et al. ............. 424/182.1 |
| 6,759,518 | B1 | | 7/2004 | Kontermann et al. |

FOREIGN PATENT DOCUMENTS

| CA | 2070233 | 12/1992 |
| CA | 2331641 | 11/1999 |
| DE | 41 18 120 A1 | 12/1992 |
| DE | 198 16 141 A1 | 10/1999 |
| DE | 198 19 846 A1 | 11/1999 |
| EP | 0 440 373 A1 | 8/1991 |
| WO | WO 94/13806 | 6/1994 |
| WO | WO 97/47271 | 12/1997 |

OTHER PUBLICATIONS

Erfurt et al., 2007, J. Immunol., 178: 7703-7709.*
Sifaki et al., 2006, Life 58: 606-610.*
Iida et al., Cancer Research (1995) 55: 2177-2185 (provided by Applicant).*
Smith et al., Blood (1996) 87: 1123-1133 (provided by Applicant).*
Chattopadhyay et al., Proc. Natl. Acad. Sci. U.S.A. (1992) 89: 2684-2688 (provided by Applicant).*
Boon et al., Annu. Rev. Immunol., 2006, 24: 175-208.*
Nielsen et al., 2000, Cancer Chemother. Pharmacol., 46 (Suppl.): S62-S66.*
Lee et al., 1999, J. Immunol., 163: 6292-6300.*
Grosse-Hovest et al., 2005, Int. J. Cancer, 117: 1060-1064 (provided by Applicant).*
International Search Report for application PCT/EP02/12545.
International Preliminary Examination Report for application PCT/EP02/12545.
Amersham Biosciences, RPAS Purification Module, Instructions, (1996).
Aruffo et al., "Molecular Cloning of a CD28 cDNA by a High-Efficiency COS Cell Expression System" *Proc. Natl. Acad. Sci. USA* 84:8573-8577 (1987).
Bischof et al., "Autonomous Induction of Proliferation, JNK and NF-xB Activation in Primary Resting T Cells by Mobilized CD28" *Eur. J. Immunol.* 30:876-882 (2000).
Bode et al., "Antibody-Directed Fibrinolysis" *Journ. of Biol. Chem.* 264:944-948 (1989).
Brandl et al., "Bispecific Antibody Fragments with CD20×CD28 Specificity Allow Effective Autologous and Allogeneic T-Cell Activation Against Malignant Cells in Peripheral Blood and Bone Marrow Cultures from Patients with B-Cell Lineage Leukemia and Lymphoma" *Experimental Hematology* 27:1264-1270 (1999).
Grosse-Hovest et al., "A Recombinant Bispecific Single-Chain Antibody Induces Targeted, Supra-Agonistic CD28-Stimulation and Tumor Cell Killing" *Eur. J. Immunol.* 33:1334-1340 (2003).
Grosse-Hovest et al., "Tumor-Growth Inhibition with Bispecific Antibody Fragments in a Syngeneic Mouse Melanoma Model: The Role of Targetd T-Cell Co-Stimulation Via CD 28" *Int. J. Cancer* 80:138-144 (1999).
Grosse-Hovest et al., "Thesis Produktion und Charakterisierung Supra-Agonistischer Bispezifischer CD28-Antikorperzur Tumor-Immuntherapie" *Internationales Aktenzeichen* 2002).
Hayden et al., "Costimulation by CD28 sFv Expressed on the Tumor Cell Surface or as a Soluble Bispecific Molecule Targeted to the L6 Carcinoma Antigen" *Tissue Antigens* 48:242-254 (1996).
Jung and Muller-Eberhard, "An in-vitro Model for Tumor Immunotherapy with Antibody Heteroconjugates" *Immunology Today* 9:257-260 (1988).

(Continued)

*Primary Examiner*—Ilia Ouspenski
(74) *Attorney, Agent, or Firm*—Foley & Lardner, LLP

(57) ABSTRACT

A first bispecific antibody molecule comprises at least one binding site with a variable domain on a light chain ($V_L$) and a variable domain for the T-cell receptor CD-28, linked thereto on a heavy chain ($V_H$). The antibody molecule further comprises at least one binding site with a variable domain on a heavy chain ($V_H$) and a variable domain for a tumour antigen, linked thereto on a light chain ($V_L$). The variable domains on the heavy chains for both specificities are connected to each other by means of a peptide linker. A second bispecific antibody molecule is bivalent for CD-28 and at least monovalent for the tumour antigen.

6 Claims, 4 Drawing Sheets

OTHER PUBLICATIONS

Figure 2A:
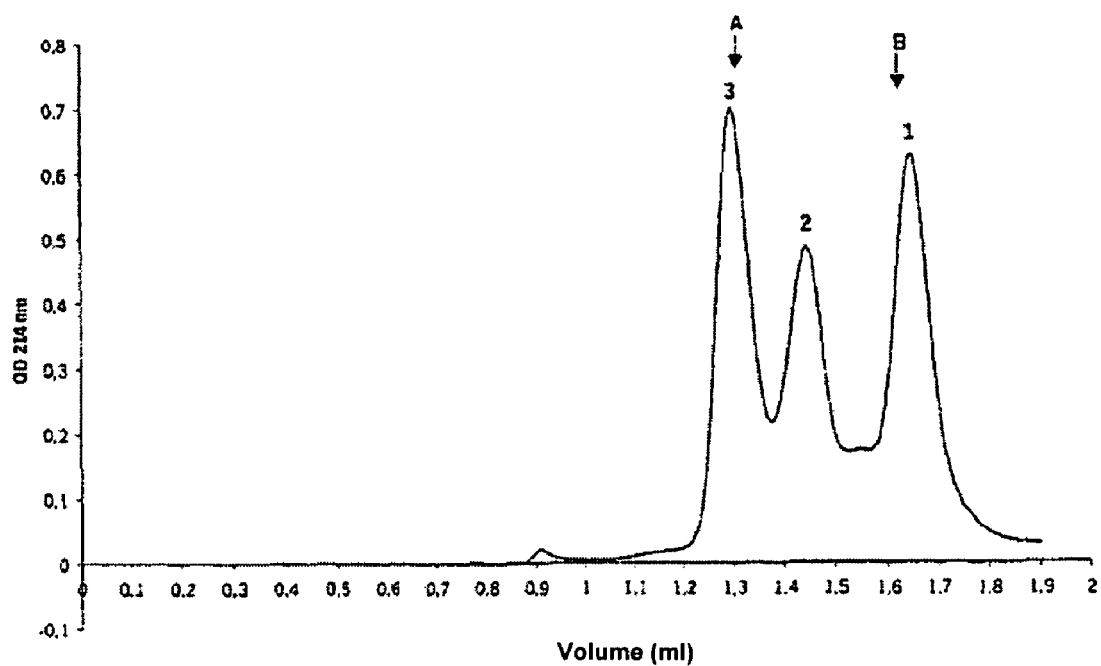

Jung et al., "Target Cell-Induced T Cell Activation with Bi- and Trispecific Antibody Fragments" *Eur. J. Immunol.* 10:2431-2435 (1991).

Kipriyanov et al., "Bispecific Tandem Diabody for Tumor Therapy with Improved Antigen Binding and Pharmacokinetics" *J. Mol. Biol.* 293:41-56 (1999).

Schoonjans et al., "Fab Chains as an Efficient Heterodimerization Scaffold for the Production of Recombinant Bispecific and Trispecific Antibody Derivatives" *Journ. of Immunol.* 165:7050-7057 (2000).

Siefken et al., "A CD28-Associated Signalig Pathway Leading to Cytokine Gene Transcription and T Cell Proliferation Without TCR Engagement" *Journ. of Immunol.* 161:1645-1651 (1998).

Tibben et al., "Pharmacokinetics, Biodistribution and Biological Effects of Intravenously Administered Bispecific Monoclonal Antibody OC/TR F(ab')$_2$ in Ovarian Carcinoma Patients" *Int. J. Cancer* 66:477-483 (1996).

Tomlinson and Holliger, "Methods for Generating Multivalent and Bispecific Antibody Fragments" *Methods in Enzymology* 326:461-479 (2000).

Van Spriel et al., "Immunotherapeutic Perspective for Bispecific Antibodies" *Review Immunology Today* 21:391-397 (2000).

Database EMBL-EBI, Accession No. AJ507107. Synthetic construct for anti-CD28 and anti-HMWG ScFv antibody, clone r28M', Sep. 2, 2002, p. 1-3.

* cited by examiner

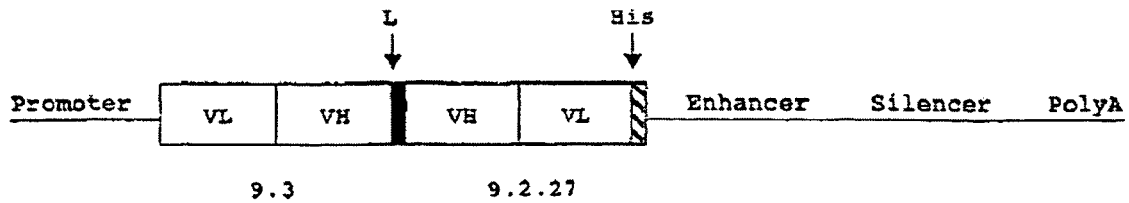

Fig. 1a

```
1    METDTLLLWV  LLLWVPGSTG  DIVLTQSPAS  LAVSLGQRAT  ISCRASESVE
51   YYVTSLMQWY  QQKPGQPPKL  LIFAASNVES  GVPARFSGSG  SGTNFSLNIH
101  PVDEDDVAMY  FCQQSRKVPY  TFGGGTKLEI  KRGGGGSGGG  GSGGGGSQVK
151  LQQSGPGLVT  PSQSLSITCT  VSGFSLSDYG  VHWVRQSPGQ  GLEWLGVIWA
201  GGGTNYNSAL  MSRKSISKDN  SKSQVFLKMN  SLQADDTAVY  YCARDKGYSY
251  YYSMDYWGQG  TTVTVSSAST  KGPSVFPLAP  SSSGSGQVKL  QQSGPELVKP
301  GASVKISCKA  SGYAFSRSWM  NWVKQRPGQG  LEWIGRIYPG  DGDTNYNGKF
351  KGKATLTADK  SSSTAYMQVS  SLTSVDSAVY  FCARGNTVVV  PYTMDYWGQG
401  TTVTVSSGGG  GSGGGGSGGG  GSDIELTQSP  ASLAVSLGQR  ATISCRASES
451  VDSYGNSFMH  WYQQKPGQPP  KLLIYLASNL  ESGVPARFSG  SGSRTDFTLT
501  IDPVEADDAA  TYYCQQNNED  PLTFGGGTKL  ELKRAAAHHH  HHH**
```

21 - 132: V$_L$ 9.3
133 - 147: FL
148 - 267: V$_H$ 9.3
268 - 286: L
287 - 407: V$_H$ 9.2.27
408 - 422: FL
423 - 543: V$_L$ 9.2.27

Fig. 1b

SEQUENCE LISTING

<160> NUMBER OF SEQ ID NOS: 3

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Linker
      peptide

<400> SEQUENCE: 1

Gly Gly Gly Gly Ser Gly Gly Gly Gly Ser Gly Gly Gly Gly Ser
 1               5                  10                  15

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Linker
      peptide

<400> SEQUENCE: 2

Ala Ser Thr Lys Gly Pro Ser Val Phe Pro Leu Ala Pro Ser Ser
 1               5                  10                  15

Gly Ser Gly

<210> SEQ ID NO 3
<211> LENGTH: 543
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 3

Met Glu Thr Asp Thr Leu Leu Leu Trp Val Leu Leu Leu Trp Val Pro
 1               5                  10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Glu Ser
            35                  40                  45

Val Glu Tyr Tyr Val Thr Ser Leu Met Gln Trp Tyr Gln Gln Lys Pro
        50                  55                  60

Gly Gln Pro Pro Lys Leu Leu Ile Phe Ala Ala Ser Asn Val Glu Ser
 65                  70                  75                  80

Gly Val Pro Ala Arg Phe Ser Gly Ser Gly Ser Gly Thr Asn Phe Ser
                85                  90                  95

Leu Asn Ile His Pro Val Asp Glu Asp Asp Val Ala Met Tyr Phe Cys
                100                 105                 110

Gln Gln Ser Arg Lys Val Pro Tyr Thr Phe Gly Gly Gly Thr Lys Leu
            115                 120                 125

Glu Ile Lys Arg Gly Gly Gly Gly Ser Gly Gly Gly Gly Ser Gly Gly
        130                 135                 140

Gly Gly Ser Gln Val Lys Leu Gln Gln Ser Gly Pro Gly Leu Val Thr
145                 150                 155                 160

Pro Ser Gln Ser Leu Ser Ile Thr Cys Thr Val Ser Gly Phe Ser Leu
                165                 170                 175

Ser Asp Tyr Gly Val His Trp Val Arg Gln Ser Pro Gly Gln Gly Leu

-continued

```
                180                 185                 190
Glu Trp Leu Gly Val Ile Trp Ala Gly Gly Thr Asn Tyr Asn Ser
            195                 200                 205
Ala Leu Met Ser Arg Lys Ser Ile Ser Lys Asp Asn Ser Lys Ser Gln
        210                 215                 220
Val Phe Leu Lys Met Asn Ser Leu Gln Ala Asp Asp Thr Ala Val Tyr
225                 230                 235                 240
Tyr Cys Ala Arg Asp Lys Gly Tyr Ser Tyr Tyr Ser Met Asp Tyr
                245                 250                 255
Trp Gly Gln Gly Thr Thr Val Thr Val Ser Ser Ala Ser Thr Lys Gly
                260                 265                 270
Pro Ser Val Phe Pro Leu Ala Pro Ser Ser Gly Ser Gly Gln Val
            275                 280                 285
Lys Leu Gln Gln Ser Gly Pro Glu Leu Val Lys Pro Gly Ala Ser Val
        290                 295                 300
Lys Ile Ser Cys Lys Ala Ser Gly Tyr Ala Phe Ser Arg Ser Trp Met
305                 310                 315                 320
Asn Trp Val Lys Gln Arg Pro Gly Gln Gly Leu Glu Trp Ile Gly Arg
                325                 330                 335
Ile Tyr Pro Gly Asp Gly Asp Thr Asn Tyr Asn Gly Lys Phe Lys Gly
                340                 345                 350
Lys Ala Thr Leu Thr Ala Asp Lys Ser Ser Thr Ala Tyr Met Gln
        355                 360                 365
Val Ser Ser Leu Thr Ser Val Asp Ser Ala Val Tyr Phe Cys Ala Arg
    370                 375                 380
Gly Asn Thr Val Val Pro Tyr Thr Met Asp Tyr Trp Gly Gln Gly
385                 390                 395                 400
Thr Thr Val Thr Val Ser Ser Gly Gly Gly Ser Gly Gly Gly Gly
                405                 410                 415
Ser Gly Gly Gly Ser Asp Ile Glu Leu Thr Gln Ser Pro Ala Ser
                420                 425                 430
Leu Ala Val Ser Leu Gly Gln Arg Ala Thr Ile Ser Cys Arg Ala Ser
        435                 440                 445
Glu Ser Val Asp Ser Tyr Gly Asn Ser Phe Met His Trp Tyr Gln Gln
        450                 455                 460
Lys Pro Gly Gln Pro Pro Lys Leu Leu Ile Tyr Leu Ala Ser Asn Leu
465                 470                 475                 480
Glu Ser Gly Val Pro Ala Arg Phe Ser Gly Ser Gly Ser Arg Thr Asp
                485                 490                 495
Phe Thr Leu Thr Ile Asp Pro Val Glu Ala Asp Ala Ala Thr Tyr
                500                 505                 510
Tyr Cys Gln Gln Asn Asn Glu Asp Pro Leu Thr Phe Gly Gly Gly Thr
        515                 520                 525
Lys Leu Glu Leu Lys Arg Ala Ala Ala His His His His His His
    530                 535                 540
```

BISPECIFIC ANTIBODY MOLECULE

CROSS-REFERENCE TO RELATED PATENT APPLICATIONS

This application claims priority to German Application 20120897.0, filed Dec. 18, 2001, which is a national stage of US Application PCT/EP02/12545, filed Nov. 12, 2001. Both applications including the specification, drawings, claims and abstract are incorporated herein by reference in their entirety.

The present invention relates to a bispecific antibody molecule, a bispecific antibody molecule with bivalence for CD28, nucleic acids coding for the antibody molecule, the antibody molecule and/or cells containing the nucleic acid coding for the antibody molecule and the use of the bispecific antibody molecule.

In the simplest case, natural antibodies are Y-shaped, tetrameric glycoproteins. Their typical structure consists of two identical light chains and two identical heavy chains. The light chain is composed of two domains $V_L$ and $C_L$, but the heavy chain is composed of the four domains $V_H$, $C_H1$, $C_H2$ and $C_H3$. The letters C and V indicate the constant and variable parts of the antibody. Disulphide bridges join the two heavy chains together, as well as the heavy to the light chains.

"Recombinant antibodies" generally means antigen-binding fragments of an antibody that is produced by a heterologous source. $F_v$ fragments that contain the variable domains of the heavy and light chain are the smallest antibody unit that can still bind an antigen.

The so-called single-chain $F_v$ fragments ($scF_v$) are often used in research and therapy. In these $scF_v$ fragments the variable domain of the heavy chain is bound covalently to the variable domain of the light chain via a short peptide spacer. This spacer is introduced at the genetic level. The $scF_v$ fragments can be purified and detected by adding short marker sequences either at the N-terminus or at the C-terminus.

The bispecific antibodies, in which antigen binding sites against two different antigens are joined together, play an important role among the recombinant antibodies. Various strategies are available for producing bispecific recombinant antibody fragments.

For example, two different $scF_v$ fragments can be joined by introducing an additional linker between the C-terminus of the first $scF_v$ fragment and the N-terminus of the second $scF_v$ fragment. If two identical $scF_v$ fragments are used, antibodies are obtained that are bivalent with respect to a binding site, and if two different $scF_v$ fragments are used, fragments are generated that are monovalent with respect to a binding site, but are at the same time bispecific, since they have two different binding sites.

In order to produce so-called diabodies, a very short linker is chosen between the variable domain of the heavy chain and the variable domain of the light chain, to prevent the $V_H$ and $V_L$ domains of a chain joining together. This can lead to the formation of dimeric molecules, in which the $V_H$ and $V_L$ domains of two different chains form a double-headed molecule. By using two different, noncoupled antibody specificities (e.g. A and B), which are expressed in the order $V_{HA}$-$V_{LB}$ and $V_{HB}$-$V_{LA}$ in the same cell, bispecific diabodies can be formed. These dimeric diabody molecules can also be produced via a monomeric molecule, if the two $V_H$-$V_L$ fragments are bound covalently with an additional peptide linker (single-chain diabody, scDb). These dimeric bispecific antibodies thus possess two valences for each specificity.

Bispecific diabodies or antibodies have been generated in order to increase both the valence as well as the stability and therefore the therapeutic potential. To date, it has been shown that in particular the binding strength could be improved by single-chain diabodies.

Tomlinson and Holliger, "Methods for Generating Multivalent and Bispecific Antibody Fragments", Methods in Enzymology (2000) 326:461-479, describe the production of bispecific diabodies. These bispecific diabodies proved effective in the recruitment of cytotoxic T-cells, of complement and of the antibody-dependent effector functions, for example cell-mediated cytotoxicity and phagocytosis.

Kipriyanov et al., "Bispecific Tandem Diabody for Tumor Therapy with improved Antigen Binding and Pharmacokinetics" J. Mol. Biol. (1999) 293:41-56, describe a diabody formation of a single-chain molecule with four V-regions of two different specificities. At the same time the team describes a dimerization of this single-chain antibody and a bispecific tandem diabody, respectively. The tandem diabodies are thus bivalent for each specificity, in the present publication for CD19 and CD3. The tandem diabodies did indeed display increased affinity for their antigen, but an associated increased biological activity could not be demonstrated. Thus, these tandem diabodies only possessed slightly increased activity with respect to the killing of tumor cells in comparison with the single-chain diabodies.

For naive T cells to be able to take part in an adaptable immune response, they must be activated for proliferation and differentiation. This activation of naive T cells takes place by the recognition of a foreign peptide fragment with the antigen-specific T cell receptor CD3-complex. It is generally recognized that the effective activation of naive T cells to proliferation and differentiation requires a second or co-stimulating signal in addition to the antigen-specific stimulus via the TCR/CD3 complex. The best-characterized co-stimulator molecules for antigen-presenting cells are the glycoproteins B7.1 and B7.2. The receptor for B7 molecules on T cells is CD28, and ligation of CD28 by B7 molecules (or by anti-CD28 antibodies) costimulates the growth of naive T cells. Following activation of the T cells, the expression of CD28 is also increased.

In the meantime, yet other costimulating receptors have been identified, but so far the B7/CD28 interaction is by far the strongest costimulus for naive T cells.

On naive, resting T cells, CD28 is the only receptor for B7 molecules. However, as soon as the cells are activated, they express the additional receptor CTLA-4. CTLA-4 binds B7 molecules far more strongly than CD28 and delivers negative signals to the activated T cells, so that, among other things, less interleukin-2 is formed. Accordingly, therapeutic use of B7 proteins as costimulating molecules proved doubtful, because the CTLA-4 receptor expressed by B7-activated T cells suppresses T cell activation.

Stimulation of the TCR/CD3 complex with bispecific antibodies induced serious and unexpected side-effects in systemic in vivo applications in humans (Tibben et al.: "Pharmacogenetics, biodistribution and biological effects of intravenously administered bispecific monoclonal antibody OC/TR Fab$_2$ in ovarian carcinoma patients", (1996) Int. J. Cancer 66:447-483).

Some years ago it was shown in various publications that chemically hybridized bispecific antibodies directed against tumor-associated antigens and against CD28 induce a T cell costimulation directed against tumor cells in vitro and in vivo: see for example Jung, G. and Müller-Eberhard, H.J.: "An in vitro model for tumor immunotherapy with antibody heteroconjugates" Immunology Today (1988) 9:257-260; Große-Hovest, L. et al.: "Tumor growth inhibition with bispecific antibody fragments in a syngeneic mouse melanoma model: The role of targeted T cell costimulation via CD28" Int. J. Cancer (1999) 80:138-144.

In the experiments these bispecific antibodies were used in combination with bispecific antibodies that stimulate the TCR/CD3 complex. Used alone, they were only slightly effective.

In 1996, Hayden et al., "Costimulation by CD28sFv expressed on the tumor cell surface or as a soluble bispecific molecule targeted to the L6 carcinoma antigen" Tissue Antigen (1996) 48:242-254, were able to show that transfected CD28 single-chain antibodies and a recombinant bispecific antibody with tumor/CD28 specificity could provoke similar costimulating effects in T cell blasts, where the blasts had already been stimulated to proliferation by phytohemagglutinin. However, the single-chain scFv molecule described is not supra-agonistic.

Against this background, the present application is based on the problem of providing a reagent that can effectively stimulate T cells supra-agonistically, i.e. without an additional costimulating signal.

This problem is solved according to the invention with a first bispecific antibody molecule with a binding site for the T cell receptor CD28 that has a variable domain of a light chain ($V_L$) and, bound thereto, a variable domain of a heavy chain ($V_H$), and with a binding site for a tumor-antigen having a variable domain of a heavy chain ($V_H$) and, bound thereto, a variable domain of a light chain ($V_L$), and the variable domains of the heavy chains are joined together by a peptide linker.

The problem is also solved with a second bispecific antibody molecule with specificity for the T cell receptor CD28 and specificity for a tumor antigen, where the bispecific antibody molecule is bivalent for CD28.

On the whole it is preferred if the binding site for the T cell receptor CD28 binds to the human T cell receptor CD28. Its sequence was published for example in Aruffo A. et al., Proc. Natl. Acad. Sci. U.S.A. 84:8573-8577 (1987).

The problem is moreover solved with a method for the treatment of cells, in which the first or second bispecific antibody molecule according to the invention is used in order to effect a supra-agonistic tumor-cell-induced activation of T cells, so that no additional exogenous stimuli are required.

The problem forming the basis of the invention is solved completely in this way.

Thus, the inventors of the present application were able to show that it is possible, just by activating the costimulator receptor CD28 by means of a bispecific antibody molecule according to the invention or by means of a dimer of the first bispecific antibody molecule according to the invention, to stimulate T cells effectively, without requiring a further antigen-specific stimulus via the TCR/CD3 complex. That means, for example, that this process takes place in a directed manner on the surface of tumor cells.

At the same time, any stimulation of CTLA-4 molecules on the activated T cells is avoided. Avoidance of stimulation of these suppressing molecules does not restrict the proliferation of the T cells, so that an appropriate immune response is not suppressed.

In other words, the T cells are activated when the bispecific antibody molecule binds the CD28 molecule on the T cells bivalently and at the same time, with its other binding site, binds to the tumor antigen on a tumor cell. There is, as it were, tumor-cell-induced, supra-agonistic activation of T cells, in which the bispecific antibody molecule according to the invention is able to stimulate the T cells effectively without an additional signal, if in addition to the CD28 molecule it has also bound to the tumor antigen. There is therefore selective, tumor-cell-induced activation of T cells, in which no binding to the TCR/CD3 complex is required.

The inventors of the present application have further shown, in various experiments of their own, that the bispecific antibody molecules were extremely effective with regard to the destruction of tumor cells.

The inventors found that, in the case of recombinant production, the first antibody molecule tends to form dimers spontaneously, and that the dimers stimulate T cells particularly efficiently on account of their bivalence for CD28. The dimers can also be generated deliberately. Since the bivalence for CD28 is produced by the supra-agonistic properties of the new antibody molecule, the second antibody molecule also displays this supra-agonistic action, for it too is bivalent for CD28, whereas it can be mono- or bivalent for the tumor antigen.

In one embodiment, the first bispecific antibody molecule is therefore bound to a further first bispecific antibody molecule to give a dimer.

On the basis of their own experiments, the inventors showed that, surprisingly, first bispecific antibody molecules according to the invention undergo dimerization. Dimerization of an antibody molecule constructed in this way had not been described before and so was entirely unexpected.

As a result of the dimerization, the bispecific antibody molecule has two binding sites for CD28 and two binding sites for the tumor antigen. With the said antibody molecule, the inventors were able to demonstrate effective tumor-cell-induced activation of T cells, which led to efficient killing of tumor cells that expressed the tumor antigen.

In a further embodiment of the first antibody molecule, furthermore at least one part of a fos-jun adaptor or of a hinge region can be fused to one of the light chains.

By fusing-on a fos-jun adaptor, dimerization can be brought about deliberately, since the gene products of the fos-jun adaptor associate spontaneously.

A "hinge region" means the segment of the heavy chain of an immunoglobulin that is arranged between the first and second constant domains. This measure, too, leads to purposeful dimerization.

An application of these functional units and examples of their sequences are for example summarized by van Spriel et al.: "Immunotherapeutic Perspective for Bispecific Antibodies" Immunol. Today (2000) 21(8):391-397.

Generally it is preferred if the tumor antigen is selected from the group comprising melanoma-associated proteoglycan, HER-2/new or CD20.

HER-2/new is an oncogene and plays an important role, especially in breast cancer. CD20 is an antigen, which is found in particular on tumor cells of the B-cell type.

These tumor antigens are only enumerated as examples, the invention also encompasses other cell surface molecules that are tumor-associated.

It is also preferable if the peptide linker on the first antibody molecule has at least one part of the N-terminus of the $C_H1$ domain of human IgG.

It is especially preferred if the part of the N-terminus of the $C_H1$ domain of the human IgG contains the amino acid sequence Ala-Ser-Thr-Lys-Gly-Pro-Ser-Val-Phe-Pro-Leu-Ala-Pro-Ser-Ser-Ser-Gly-Ser-Gly (SEQ ID NO: 2).

In one embodiment of the second antibody molecule, an scFv fragment with CD28 specificity is fused to each of the two constant domains of a Fab fragment with anti-tumor specificity.

With this construction, an antibody molecule is created that is bivalent for CD28 and monovalent for the tumor antigen.

A construction of this type but with different specificities is described for example by Schoonjans, R. et al.: "Fab Chains as an Efficient Heterodimerization Scaffold for the Production of Recombinant Bispecific and Tri-specific Antibody Derivatives", J. Immunol. (2000) 165(12):7050-7057.

In a further embodiment, the second bispecific antibody molecule is also bivalent for the tumor antigen.

The bispecific antibody molecule according to the invention is bivalent for CD28 and mono- or bivalent for the tumor antigen, with the aforementioned supra-agonistic action being achieved by the bivalence for CD28, as a result of which the T cells are stimulated without any additional signal, but only when, in addition to the bivalent binding to the CD28 molecule on the T cell, there is also mono- or bivalent binding to the tumor antigen on the tumor cell.

In a further embodiment of the second antibody molecule, an scFv fragment with CD28 specificity is fused to each of the heavy chains of a complete antibody with anti-tumor specificity.

A "complete" antibody means an antibody that possesses the structure of an immunoglobulin. These contain two heavy chains in each case with one variable and three constant domains and two light chains each with one variable and one constant domain.

Through the fusing in each case of an scFv fragment with CD28 specificity to the said complete antibody molecule with anti-tumor specificity, a bispecific antibody molecule is created that is bivalent both for CD28 and for a tumor antigen.

A construction of this type but with different specificities and their functionality is described for example in van Spriel et al.: "Immunotherapeutic Perspective for Bispecific Antibodies", Immunol. Today (2000) 21(8):391-397.

The invention further relates to a nucleic acid that codes for a bispecific antibody molecule according to the invention. The nucleic acid is generally a DNA or an RNA, preferably double-stranded DNA.

A further object of the invention is a vector, which encompasses the nucleic acid according to the invention. The said vector can be a viral or a non-viral vector.

In one embodiment of the invention, the nucleic acid or the vector is expressed in a cell. The cell can comprise from the group comprising mammalian, bacterial, insect, plant or yeast cells. The cell transformed or transfected with the nucleic acid according to the invention or the vector according to the invention is cultivated and the gene product expressed is then isolated.

A further object of the invention is a pharmaceutical composition with a bispecific antibody molecule according to the invention and a pharmaceutically acceptable carrier.

The bispecific antibody molecule according to the invention can be used for tumor-cell-induced T cell activation, especially in the therapy and/or prophylaxis of tumor diseases, in order to destroy the tumor cells selectively by activating the T cells that express the tumor antigen. Selective destruction of tumor cells can be effected for example in vitro by incubating T cells and the tumor cells expressing the tumor antigen together with the bispecific antibody molecule according to the invention. In vivo, selective destruction of tumor cells can be effected by administering a medicinal product that contains the bispecific antibody molecule. The said molecule then binds on the one hand with its binding site for the tumor antigen to the tumor cell thus defined and on the other hand to T cells that are present in the body, namely via the bivalent binding site for the CD28 molecule, which is expressed on the T cells. Since further stimulation of the T cells via the TCR/CD3 complex is not required, in this supra-agonistic manner there is tumor-cell-induced activation of the T cells and therefore selective destruction of the tumor cells.

In the case of human T cells, a TCR/CD3-independent activation has indeed been observed when using a specially immobilized CD28 antibody (BW828), but this proved to be only moderate, and the 9.3 (CD28) antibody that was also used in examples of application of the present application was found to be only extremely slightly effective in the activation of T cells: see Siefken et al.: "A CD28 associated signaling pathway leading to cytokine gene transcription and T cell proliferation without TCR engagement" J. Immunol. (1998) 161:1645-1651 and in the references there. This confirms that the antibody only becomes supra-agonistic in bispecific form, i.e. after binding to the target antigen. In this sense the supra-agonistic action is selective.

Bischof et al., "Autonomous induction of proliferation, JNK and NFalphaB activation in primary resting T cells by mobilized CD28" Eur. J. Immunol. (2000) 30(3):876-882, were in fact able to show that antibodies to rat CD28 stimulated T cell proliferation without additional TCR-CD3, but this effect was attributed to the special CD28 antibodies, specifically for immobilized CD28 for shortening the TCR/CD3-independent CD28 recruitment. Besides, these studies with monospecific CD28 antibodies do indeed describe supra-agonistic effects, but not those that are triggered selectively by binding to a target antigen.

Further advantages can be seen from the description and the appended drawing.

Of course, the characteristic features stated above and those yet to be explained below can be used not only in the combination stated in each case, but also in other combinations or on their own, without leaving the scope of the present invention.

Figure 2B:
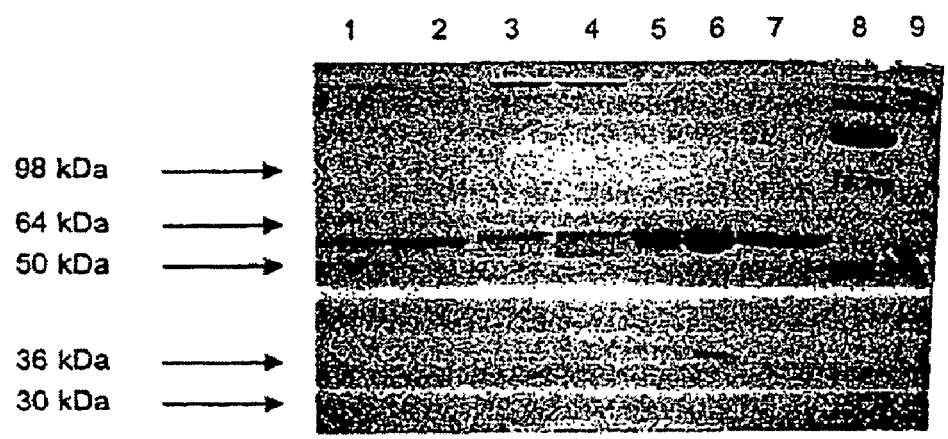
Figure 3:
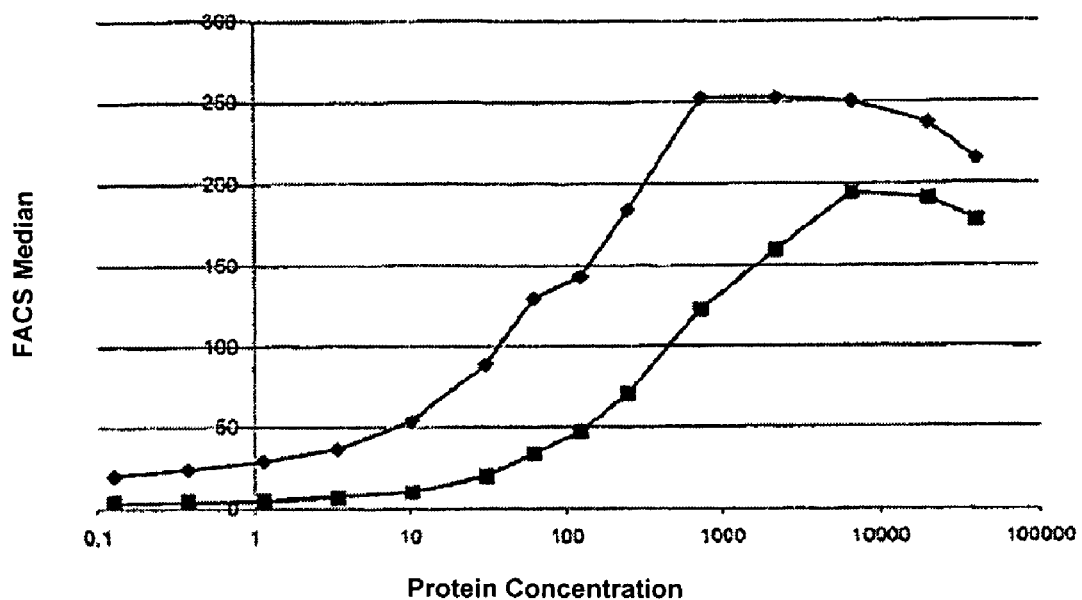
Figure 4:
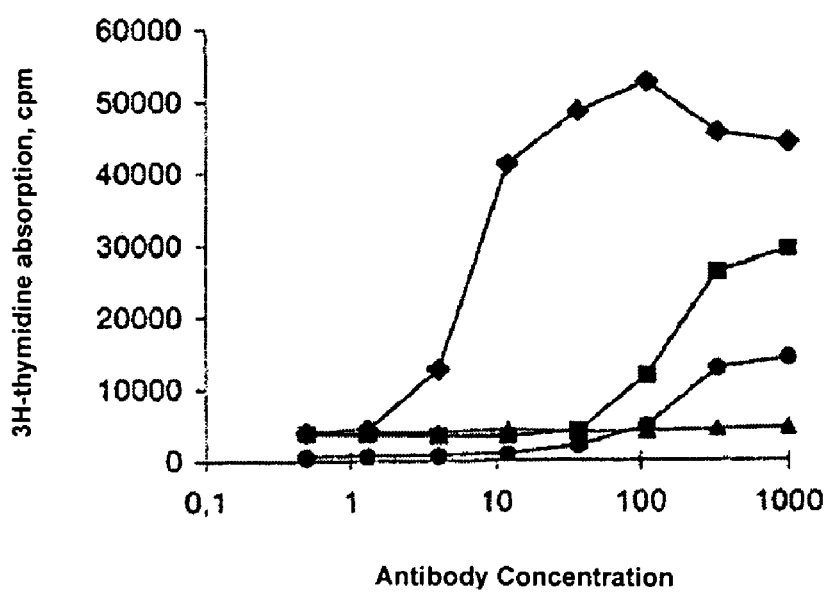
Figure 5:
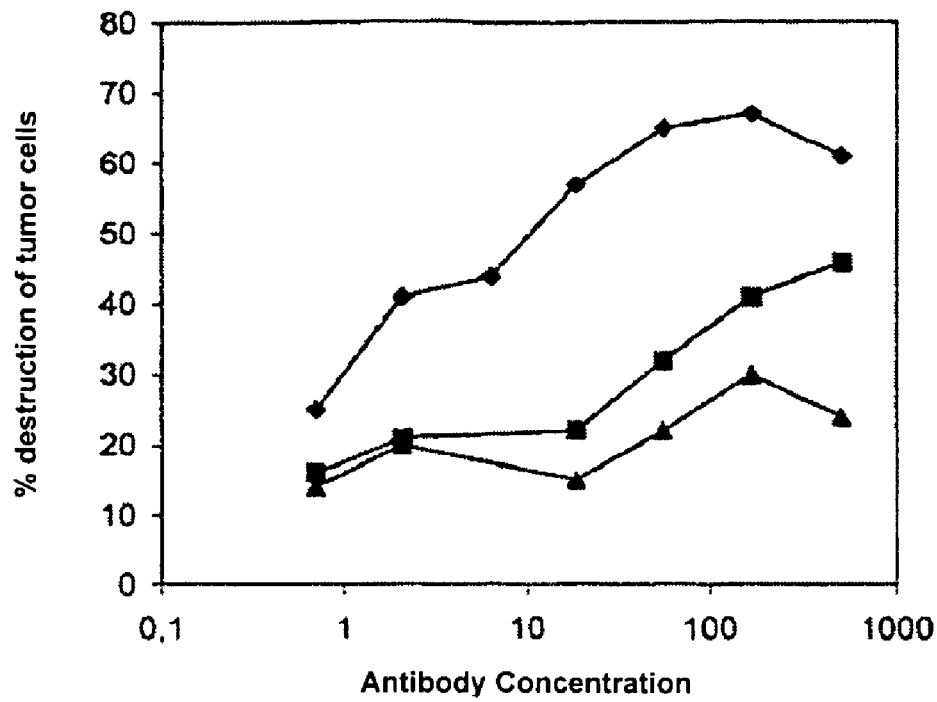
Figure 6:
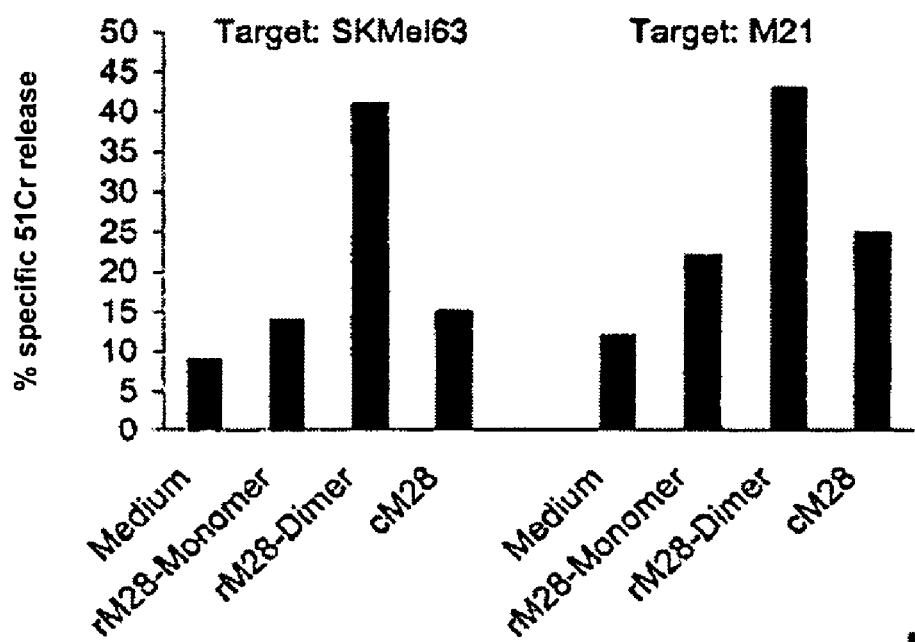

Embodiments of the invention are shown in the drawing and are explained in more detail in the description hereunder. The following are shown:

FIG. 1a a schematic representation of the first antibody molecule at the genetic level;

FIG. 1b the amino acid sequence (SEQ ID NO: 3) of a first bispecific antibody molecule according to the invention;

FIG. 2a the purification of the recombinant antibody by gel filtration;

FIG. 2b the fractions from gel filtration, separated by SDS-polyacrylamide gel electrophoresis;

FIG. 3 the binding activity of the monomeric and dimeric recombinant single-chain antibody with CD28/9.2.27 specificity on Jurkat T-cell lymphoma cells;

FIG. 4 activation of peripheral-blood mononuclear cells (PBMC) by irradiated SKMel63 cells that had been incubated for three days with the recombinant antibody dimer or the recombinant antibody monomer;

FIG. 5 killing of SKMel63 cells after incubation for four days with peripheral-blood mononuclear cells (PBMC) and the recombinant antibody as monomer or as dimer;

FIG. 6 lysis of the SKMel63 and M21-melanoma cells by peripheral-blood mononuclear cells (PBMC) that had been incubated with SKMel63 cells.

EXAMPLE 1

Genetic Construction and Expression of the Single-chain, Bispecific Antibody Molecule The monospecific $scF_v$ antibodies were obtained from hybridoma cDNA using the RPAS system (Pharmacia Biotech, Freiburg). The variable chains $V_L$ and $V_H$ in each case of one specificity are joined together by a flexible 15-amino acid linker, which has the following amino acid sequence:

(SEQ ID NO:1)
(Gly-Gly-Gly-Gly-Ser)$_3$

After production of the functional monospecific scF$_v$ fragments, these were joined together by a 19-amino acid linker. This linker L corresponds to a part of the N-terminus of the C$_H$1 domain of human IgG. The amino acid sequence of linker L is as follows:

(SEQ ID NO:2)
Ala-Ser-Thr-Lys-Gly-Pro-Ser-Val-Phe-Pro-Leu-Ala-Pro-Ser-Ser-Ser-Gly-Ser-Gly.

In this way a construct was generated with the following 5'→3' orientation:

(V$_L$-FL-V$_H$)$_{9.3}$-L-(V$_H$-FL-V$_L$)$_{9.2.27}$-6his.

In each case V$_L$ denotes the variable domain of the light chain, and V$_H$ the variable domain of the heavy chain. The "9.3" antibody fragment is specific for CD28, and the "9.2.27" antibody fragment is specific for melanoma-associated proteoglycan. The amino acid sequences of the antibody fragments are shown in FIG. 1b. The light chain V$_L$ 9.3 is preceded by a leader sequence for expression of the antibody molecule in the culture supernatant. "L" denotes the peptide linker that joins the two specificities, and "FL" represents the 15-amino acid-long, flexible linker in each case between the heavy and the light chain of one specificity. An amino acid residue with six histidines is given as "6his", and it is also designated as His-Tag.

As regulating elements, on the one hand a 1.1 kB κ-promoter fragment was fused to the 5'-end of the coding region, at the 3'-end a 5.5 kB μ-intron, which contains an enhancer fragment ("enhancer"), and a 1.8 kB long PolyA tail ("PolyA") was added (see FIG. 1a). This construct was cloned into a vector, which was produced by fusion of pCDNA-3 (Stratagene, La Jolla, Calif.) and of the pCR-Script vector (Invitrogen, Groningen, The Netherlands). The genetic organization of the antibody molecule is shown schematically in FIG. 1a (not to scale).

Next, two mouse myeloma cell lines, P3X63Ag8 and J558, were transfected with the construct by electroporation. The production rates achieved with the J558 cell line were greater than those of the other cell lines, therefore this was used for purification of the recombinant antibody.

Instead of the spontaneous dimerization described here, of the first bispecific antibody molecule during its recombinant production, the dimerization can also be effected in a targeted manner. It is moreover possible, using recombinant technology, to produce second antibody molecules according to the invention that are bivalent for CD28 and mono- or bivalent for a tumor antigen and, like the dimers from the first antibody molecules according to the invention, effectively stimulate T cells.

EXAMPLE 2

Purification of the Recombinant Antibody

In a first purification step, the ammonium sulfate-precipitated supernatant of transfected cells was applied to a protein-L column. Protein-L binds particular Vκ subtypes of the light chains of the mouse. Three definite peaks could be identified during gel filtration, which corresponded to a molecular weight of approx. 55,000 (peak 1), 100,000 (peak 2) and 160,000 (peak 3) dalton (see FIG. 2a). Gel filtration was carried out on Superdex S200 columns (Pharmacia, Freiburg, Germany), either with conventional FPLC equipment for preparative separation, or with the SMART system (Pharmacia) for analytical gel filtration.

Conversely, after SDS-polyacrylamide gel electrophoresis (SDS-PAGE) only two bands could be observed, which corresponded to a molecular weight of approx. 55,000 and 160,000 dalton, as shown in FIG. 2b: In trace 6, the ammonium sulfate-precipitated supernatant of transfected cells was applied before gel filtration. In trace 1 the peak-1 material was applied after gel filtration. In trace 2, the peak-2 material is shown after gel filtration and after protein-G adsorption, and in trace 3, peak-2 material after gel filtration and before protein-G adsorption. The molecular weight analyses were carried out by a 10% SDS-PAGE. Protein-G and protein-L material from the company Devitron (Castrop-Rauxel, Germany) was used.

In view of the fact that the band with a weight of 160 kilodalton could be removed by adsorption on protein-G, this band could be identified as immunoglobulin, which had been produced by the transfected cell line J558 itself.

The purified material from peak 2 of cell lines J558 and P3X63Ag8 could not be distinguished from the peak-1 material after SDS-PAGE: both of the antibody species contained in the two peaks possessed a molecular weight of approximately 58 kilodalton, which was in agreement with the expected molecular weight of the monomeric bispecific single-chain molecule.

Furthermore, the two antibody species proved to be identical in the N-terminal protein sequencing. The protein sequence analyses were carried out by Edman degradation in a Hewlett Packard Protein Sequencer G241 (Hewlett Packard, Waldbronn, Germany).

To summarize, it was found that an antibody species with a molecular weight of approximately 115 kilodalton could be purified by gel filtration (peak-2 material) and that this antibody appeared in SDS-PAGE with exactly half the original molecular weight, yet it had the same sequences as the expected monomeric bispecific single-chain molecule. Accordingly it could be shown that the peak-2 material has homodimers of the recombinant bispecific single-chain molecules (rM28 dimer). The dimer cannot be detected by SDS-PAGE, as it breaks down into its monomers during gel electrophoresis.

EXAMPLE 3

Binding Activities of the Various Bispecific Antibody Species

In order to determine the binding of the bispecific antibodies, Jurkat and M21 cells that express CD28 and the melanoma-associated proteoglycan were incubated with antibodies of various concentrations, washed and stained with an anti-histidine monoclonal antibody (dia 900, Dianova, Hamburg, Germany) and a goat-(anti-mouse) antibody (Dianova). The cells were analyzed in the FACSCalibur using CellQuest software (Becton Dickinson, San Jose, USA).

The binding activity of the various bispecific antibody species on Jurkat cells is shown in FIG. 3. Binding was measured both for the melanoma-associated proteoglycan and for CD28, both specificities are expressed on M21 and Jurkat T cells. As can be seen from FIG. 3, the binding behavior of the dimeric recombinant antibody (♦ dimer) was found to be improved in comparison with the monomeric single-chain antibody (■ monomer).

For comparison, chemically hybridized bispecific antibodies (cM28) were also produced: antibodies that possessed either melanoma (9.2.27)-specificity or CD28 (9.3)-specificity, were isolated from hybridoma supernatants by protein A column chromatography. The antibodies were fragmented and hybridized by selective reduction and re-oxidation of disulphide bridges of the hinge region. The method of chemical hybridization is described for example by Jung et al.: "Target cell induced T cell activation with bi- and trispecific antibody fragments" Eur. J. Immunol. (1991) 21:2431-2435. With the reaction conditions used, it was possible to avoid the formation of homodimers. The bispecific antibodies chemically hybridized in this way displayed a similar binding affinity as the monomeric antibodies in the binding assays (data not presented).

EXAMPLE 4

Target-cell-induced T Cell Activation

In order to measure target-cell-induced T cell activation, both the monomeric and the dimeric bispecific tumor/CD28 antibodies were incubated three times in 96-well microtiter plates with irradiated (120 Gy) SKMel63 cells ($10^4$/well) and peripheral-blood mononuclear cells (hereinafter: PBMC) from healthy donors ($10^5$/well). During the last 18 hours of a 4-day incubation period, $^3$H-thymidine was added (0.5 µCi/well). The cells were harvested and the radioactivity was determined in a scintillation counter (MicroBeta, Wallac).

FIG. 4 shows the induction of T cell proliferation by the various bispecific antibody constructs in the presence of SKMel63 melanoma cells, to which the antibodies bind specifically: the chemically hybridized F(ab')$_2$ fragment (▲cM28) proved to be moderately effective even at a high antibody concentration. In contrast, the recombinant dimeric molecules (♦ rM28 dimer) induced cell activation which is comparable to stimulation with phytohemagglutinin (PHA), even at concentrations of 10 ng/ml. The monomer (■ rM28 monomer) displayed a certain activity at high concentrations, and this activity increased with the storage time. T cell activation by the rM28 dimer in the absence of SKMel63 target cells is shown by the curve with the symbol ●. In two out of six independent tests, cM28 showed low activity at concentrations of >300 ng/ml. Apart from these exceptions, the experiment shown in FIG. 4 is representative.

When initially monomeric material was analyzed again by gel filtration after a storage time of two weeks at 4° C., it was found that more than 15% of the material was in the dimeric form. Therefore at least some part of the monomer activity can be attributed to the fact that small amounts of contaminating dimer were either already present at the beginning of the assay or were formed spontaneously as it progressed.

In some experiments the dimeric molecule, but not the monomeric (rM28-monomer) or the bispecific F(ab')$_2$ fragment (cM28), displayed a certain background activity, i.e. induction of T cell activation without target cells being present. However, this activity was always significantly lower than that observed in the presence of melanoma cells, and the activity always only arose at a high antibody concentration. When UvGG was used as control, a proteoglycan-negative "ovarian cancer" carcinoma cell line, T cell activation did not take place beyond this background level.

T cell activation going beyond this background level also was not found with the antigen-negative cells T98G and U373.

EXAMPLE 5

Killing of Tumor Cells

For determining the killing of tumor cells, viable melanoma cells were incubated together with PBMC and antibodies three times in 96-well microtiter plates ($5 \times 10^3$/well). After four days the PBMC were removed and the number of the remaining viable, adhering tumor cells was determined after staining with the tetrazolium salt WST (Roche Diagnostics, Mannheim, Germany). The optical density was determined in an ELISA reader (Spectra Max 340, Molecular Devices, Sunnyvale, Calif.) and the percentage of killed cells was calculated.

Alternatively, the cytotoxicity of the PBMC was measured after incubation of viable tumor cells in culture bottles ($3 \times 10^4$/ml) with PBMC ($6 \times 10^5$/ml). After three days the cells, which had been stimulated in the presence of SKW63 cells, were harvested and tested in a $^{51}$Cr release assay, with stimulating SKW63 cells and M21 cells as targets. Finally both cell lines were labeled with $^{51}$Cr (40 µCi/ml) for an hour, sown on 96-well microtiter plates ($5 \times 10^3$/well) and incubated with PBMCs that had been stimulated in the presence of SKW63 and bispecific antibodies with an effector:target ratio of 30:1. The $^{51}$Cr yield was measured after four hours. The percentage of killed tumor cells was calculated using the following standard formula:

$$(cpm_x - cpm_{spont})/(cpm_{max} - cpm_{spont})$$

In the above, $cpm_{max}$ denotes the radioactivity that is released by target cells treated with detergent, and $cpm_{spont}$ denotes the spontaneous release in the absence of PBMC and antibodies.

It is shown in FIG. 5 that T cell activation leads to effective killing of tumor cells. After four days, melanoma cells that had been incubated with PBMC in the presence of the dimeric bispecific antibody were destroyed almost completely (♦ rM28-dimer). As in the proliferation assay, killing of tumor cells was significantly intensified if the dimeric (♦ rM28-dimer) recombinant bispecific antibody was used instead of the monomeric (■ rM28-monomer). The activity of the chemically hybridized bispecific antibody (▲ cM28) was again only slight.

FIG. 6 shows the lytic activity of PBMCs that had been incubated with SKMel63 for three days, with the stimulating cells and the M21 cells serving as the target in a standardized $^{51}$Cr-release assay. It is quite clear that the dimeric recombinant antibody is the most effective in induction of cell lysis.

However, this activity seems to be nonspecific, because not only the stimulating cells, but also a melanoma cell with different HLA type was killed. Therefore the lytic activity that was measured under these conditions should not be ascribed to alloreactive T cells.

To summarize, it can be said that a dimer of the first bispecific antibody molecules according to the invention with CD28/tumor specificity is a promising means for effectively activating T cells with respect to a particular tumor, without the need for additional stimulation of the TCR/CD3 complex.

It is not, however, a necessary requirement that the antibody molecule should also be bivalent for the tumor antigen, what is important is bivalence for CD28.

The invention claimed is:

1. A recombinant bispecific antibody molecule with a first binding site for the CD28 molecule and a second binding site for a tumor-associated cell-surface antigen, wherein the variable domains of the respective heavy chain ($V_H$) of the two binding sites are joined together via a peptide linker that contains the amino acid sequence Ala-Ser-Thr-Lys-Gly-Pro-Ser-Val-Phe-Pro-Leu-Ala-Pro-Ser-Ser-Ser-Gly-Ser-Gly (SEQ ID NO: 2).

2. The antibody molecule as claimed in claim 1, wherein the tumor-associated cell-surface antigen is selected from the group consisting of melanoma-associated proteoglycan, HER-2/neu and CD20.

3. The antibody molecule as claimed in claim 2, wherein the tumor-associated cell-surface antigen is melanoma-associated proteoglycan.

4. The antibody molecule as claimed in one of the claims 1 to 3, which has the sequence SEQ ID NO: 3.

5. A pharmaceutical composition containing an antibody molecule as claimed in one of the claims 1 to 3 and a pharmaceutically acceptable carrier.

6. A method for treating a patient having cancer comprising administering a sufficient amount of the bispecific antibody of any of claims 1-3.

* * * * *

UNITED STATES PATENT AND TRADEMARK OFFICE
CERTIFICATE OF CORRECTION

PATENT NO. : 7,538,196 B2
APPLICATION NO. : 10/495664
DATED : May 26, 2009
INVENTOR(S) : Jung It is certified that error appears in the above-identified patent and that said Letters Patent is hereby corrected as shown below:

On the title page,

[*] Notice: Subject to any disclaimer, the term of this patent is extended or adjusted under 35 USC 154(b) by (221) days Delete the phrase "by 221 days" and insert -- by 449 days --

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,538,196 B2 Page 1 of 1
APPLICATION NO. : 10/495664
DATED : May 26, 2009
INVENTOR(S) : Gundram Jung It is certified that error appears in the above-identified patent and that said Letters Patent is hereby corrected as shown below:

On the title page, item (*) Notice should read:

Subject to any disclaimer, the term of this patent is extended or adjusted under 35 U.S.C. 154(b) by 790 days.

Signed and Sealed this

Tenth Day of August, 2010

David J. Kappos
*Director of the United States Patent and Trademark Office*

UNITED STATES PATENT AND TRADEMARK OFFICE
Certificate

Patent No. 7,538,196 B2                                                                                     Patented: May 26, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gundram Jung, Rottenburg-Wendelsheim (DE); Ludger Grosse-Hovest, Tubingen (DE); Gottfried Brem, Hilgertshausen (DE); and Wolfgang Marwan.

Signed and Sealed this Twenty-fifth Day of June 2013.

<div style="text-align:right">

DAVID E. KOLKER
*Supervisory Patent Examiner*
Art Unit 1644
Technology Center 1600

</div>

UNITED STATES PATENT AND TRADEMARK OFFICE
Certificate

Patent No. 7,538,196 B2                                                                              Patented: May 26, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gundram Jung, Rottenburg-Wendelsheim (DE); Ludger Grosse-Hovest, Tubingen (DE); Gottfried Brem, Hilgertshausen (DE); and Wolfgang Marwan, Magdeburg (DE).

Signed and Sealed this Ninth Day of July 2013.

*DANIEL KOLKER*
*Supervisory Patent Examiner*
Art Unit 1644
Technology Center 1600